United States Patent [19]

Ludescher et al.

[11] Patent Number: 5,639,877
[45] Date of Patent: Jun. 17, 1997

[54] INTERMEDIATES IN THE SYNTHESIS OF CEPHALOSPORINS

[75] Inventors: Johannes Ludescher, Breitenbach; Ingolf Macher, Wörgl, both of Austria

[73] Assignee: Biochemie Gesellschaft m.b.H., Austria

[21] Appl. No.: 281,881

[22] Filed: Jul. 28, 1994

[30] Foreign Application Priority Data

Jul. 30, 1993 [AT] Austria ................................ 1520/93

[51] Int. Cl.$^6$ ................................................ C07D 501/06
[52] U.S. Cl. .......................... 540/221; 540/222; 540/226; 540/227
[58] Field of Search ................................ 540/222, 221, 540/226, 227

[56] References Cited

U.S. PATENT DOCUMENTS 4,430,498  2/1984  Heusler et al. ........................... 544/16
4,560,749  12/1985  Spry ......................................... 540/215

FOREIGN PATENT DOCUMENTS 53077     6/1982   European Pat. Off. .
150378    8/1985   European Pat. Off. .
0127541   8/1990   European Pat. Off. .
5213968   8/1993   Japan .
403523    6/1972   Spain .
8704501   6/1987   Spain .

OTHER PUBLICATIONS

The Journal of Antibiotics vol. 45, No. 5, pp. 721–734 (1992).
Tetrahedron vol. 41, No. 22, pp. 5133–5139, 1985.
Chemical Abstracts, 14297s, vol. 114, p. 738 1991.

*Primary Examiner*—Joseph McKane
*Assistant Examiner*—Richard S. Myers, Jr.
*Attorney, Agent, or Firm*—Robert S. Honor; Melvyn M. Kassenoff; Thomas O. McGovern

[57] ABSTRACT

Novel amidine salts of 7-Amino-3-hydroxymethyl-3-cephem-4-carboxylic acid (=HACA), particular guanidine and diaza-bicyclo-alkylene salts, are useful as intermediates in the synthesis of cephalosporins.

12 Claims, No Drawings

INTERMEDIATES IN THE SYNTHESIS OF CEPHALOSPORINS

This invention relates to intermediates in the synthesis of cephalosporins. It provides in one aspect novel amidine salts of 7-Amino-3-hydroxymethyl-3-cephem-4-carboxylic acid (=HACA) which include guanidine and diaza-bicycloalkylene salts.

Particularly the invention provides a compound of formula

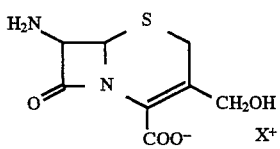

wherein $X^+$ denotes a compound of formula

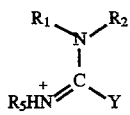

wherein Y (i) denotes a group of formula —$NR_3R_4$ and a) $R_1$ to $R_5$ are the same or different and denote independently of one another hydrogen, optionally substituted alkyl or aryl or b) two of the substituents $R_1$ to $R_5$, which are bonded to different nitrogen atoms, together form a —$(CH_2)_2$— or —$(CH_2)_3$— group and the other substituents $R_1$ to $R_5$ are as defined above (ii) denotes together with $R_2$ a —$(CH_2)_3$— or —$(CH_2)_5$— group and $R_1$ and $R_5$ denote together a —$(CH_2)_3$— group. HACA is of great interest as a starting material for highly effective cephalosporins. Position 7 thereof may be acrylated to form the corresponding 7-acylamino-3-hydroxymethyl-3-cephem-4-carboxylic acid, and likewise, the hydroxy function in position 3 and optionally the carboxylic function in position 4 may be changed to form a series of highly effective derivatives. For example, the active substances derivation to take place in position 7 and, if desired, subsequently in position 3, without either having to change a solvent or having to isolate the intermediate stage, for reasons of reactivity of the derivitisation reagents.

Surprisingly, soluble forms of HACA have been found in the form of its amidine salts, which on the one hand are stable despite the high basicity of the corresponding bases, and on the other hand are soluble in a number of solvents or solvent mixtures, and thus create many options in the synthesis of cephalosporin end products or intermediate products, depending on the reactivity and solubility of the derivitisation reagents.

Amidine means also a guanidine which has a further amine group at the carbon atom of the —N═C—N— group thus being an amino-amidine. Suitable guanidines are for example compounds of formula II, wherein Y denotes a group of formula —$NR_3R_4$ and a) $R_1$ to $R_5$ are the same or different and denote independently of one another hydrogen, optionally substituted alkyl or aryl or b) two of the substituents $R_1$ to $R_5$, which are bonded to different nitrogen atoms, together form a —$(CH_2)_2$— or —$(CH_2)_3$— group and the other substituents $R_1$ to $R_5$ are as defined above.

Any carbon containing group except where otherwise stated herein preferably contains up to 20 carbon atoms.

Preferably $R_1$ to $R_5$ denote independently of one another hydrogen, unsubstituted alkyl or alkyl substituted by a phenyl group, for example benzyl, or unsubstituted aryl.

Alkyl means preferably ($C_1$-$C_8$) alkyl, more preferably ($C_1$-$C_6$) alkyl. Aryl means preferably a group having an arylic structure such as phenyl, naphthyl or an aromatic heterocyclic radical. More preferably aryl means a phenyl group.

Alkyl and aryl may optionally be substituted by groups which are inert under the reaction conditions of the following reaction steps such as acylation and further derivitisation. Such groups are in the case of alkyl for example: aryl, as for example phenyl, nitro groups, protected hydroxy or thio groups, protected amine groups and in the case of aryl for example: alkyl, aryl, protected hydroxy or thio groups, halogen, nitro groups, protected amino groups. Protection groups are such which do not disturb the acylation reaction and further derivitisation reactions.

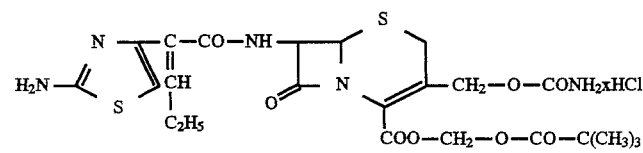

S 1108

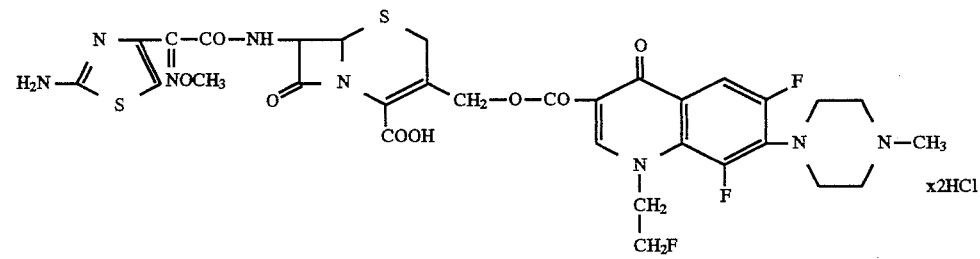

RO 23-9424 may be produced.

We have found particular forms of HACA which are particularly useful for economical synthesis in the production of such cephalosporins. These are stable soluble forms of HACA in a solvent or solvent mixture which allows Particularly useful are guanidines of formula II in which $R_1$ to $R_5$ independently of one another denote hydrogen, methyl, ethyl, benzyl or phenyl, for example tetramethyl guanidine, pentamethyl guanidine or methylphenyl guanidine, preferably tetramethyl guanidine.

Salts of HACA are known: The Na salt (Journal of Antibiotics 45/5, page 721 ff, 1992) and the triethylammonium salt (ES 403 523). In the Journal of Antibiotics, the acylation of the sodium salt of HACA with 2-(2-chloracetamidothiazol-4-yl)-2(Z)-methoximino-acetyl chloride hydrochloride is described. In this, the HACA is acylated as the sodium salt in a mixture of THF/water and the protecting group is subsequently removed. The yield is only 50% and derivitisation of the hydroxy function then takes place in a separate step. Moreover, water is a most unfavorable solvent for such a sensitive derivitisation reaction. In example 3 of ES 403 523, the triethylammonium salt of HACA is acylated without stating the solvent system, but undesired lactonisation simultaneously takes place. We have found that HACA may not be dissolved using triethyl amine in, for example, dichloromethane or methanol.

Salts of certain 7-amino-3-cephem-4-carboxylic acid derivatives with amidines and guanidines are known for example from EP 127 541, but all the β-lactam nucleii mentioned have non-reactive substituents in position 3, for example the substituent in position 3 may be a simple methyl group or a sulphur heterocycle. In contrast, HACA with its hydroxy function possesses a reactive functional group in position 3. It is known, that β-lactams are not inert towards alcohols. In addition, in the case of 3-hydroxymethyl-3-cephem-4-carboxylic acids, there is a great risk of lactonisation.

Surprisingly, the salts of HACA according to the invention are stable in solution, and in practice there is neither decomposition in the presence of the strong bases through inter-molecular nucleophilic ring opening of the β-lactam ring due to the alcohol function, nor intra-molecular lactonisation.

The salts according to the invention may be produced by e.g. bringing into contact the HACA with the corresponding amidine or guanidine preferably in a solvent. In an aprotic solvent preferably an approximately stoichiometric quantity of the amidine or the guanidine, preferably 1.0 to 1.2 equivalents are used based on the HACA employed. In protic solvents, e.g. in methanol, in order to obtain a solution, the quantity should be increased to ca. 1.5 to 2.0, e.g. to 1.8 equivalents. The salts according to the invention may be isolated by adding a non-solvent to the solution. Thus for example, the tetramethylguanidinium salt of HACA may be precipitated as a syrup from a solution in dichloromethane by adding methyl tert.butyl ether or by adding acetone to a methanolic solution. The 1,5-diaza-bicyclo[4.3.0]non-5-ene (=DBN) salt may be crystallized from chloroform, the tetramethylguanidinium salt also from dichloromethane.

Suitable solvents are e.g. the chlorinated hydrocarbons such as dichloromethane, ethers such as tetrahydrofuran, alcohols such as methanol, amides such as dimethylformamide, sulphoxides or sulphones such as sulpholane, ketones such as acetone, methyl isobutyl ketone, acetonitrile or mixtures of such solvents. Preferred solvents are dichloromethane, methanol, dimethylformamide, acetone or acetonitrile, particularly preferred are dichloromethane, methanol or acetonitrile.

In another aspect the invention provides a process for the production of cephalosporins which comprises acylating an amidine salt of 7-amino-3-hydroxymethyl-3-cephem-4-carboxylic acid in the 7-position and if necessary converting the product into other cephalosporins, particularly converting the product into a derivative from the 3-hydroxymethyl group.

In another aspect the invention provides the use of an amidine salt of 7-amino-3-hydroxymethyl-3-cephem-4-carboxylic acid in the production of cephalosporins.

The salts according to the invention may be acylated on the amino group in excellent yields. The reaction may be carried out using any conventional method for acylation, e.g. in analogous manner to that described in the Examples thereafter. Preferably the carboxylic acid used for acylating is in activated form. Suitable activated forms of carboxylic acids are the acid chlorides, (mixed) anhydrides, activated esters or a carboxylic acid-carbodiimide system. If required, in order to bind the acid being released, a base may be added, preferably an organic nitrogen base.

When the reaction has taken place, the corresponding acyl derivatives of HACA may be in situ further converted into other cephalosporins, e.g. on the hydroxy function in position 3, e.g. to produce the compounds S1108 or RO 23-9424, as necessary temporarily protecting reactive group; if desired the acyl derivatives may be isolated before. Reactions at position 3 are conventional derivitisation reactions of alcohols, e.g. ester formation with activated carboxylic acid derivatives, carbamate formation with isocyanates or nucleophilic substitution by means of an activated derivative of the alcohol and may be carried out using any suitable conventional method.

As a result of the surprising stability and solubility of the salts according to the invention in organic solvents, on the one hand there is freedom of choice of the acylation agent in order to produce the most varied N-acyl derivatives of HACA in good yields and good purity and on the other hand, if desired, the solvent (system) may be selected such that the second reaction sequence, i.e. the further derivitisation on the hydroxy function, may be carried out in the same solvent (system) as the acylation reaction in situ with sensitive reagents.

In the following Examples, which illustrate the invention more fully, but in no way limit its scope, the temperatures are given in degree celsius. The following abbreviations are used:

HACA=7-amino-3-hydroxymethyl-3-cephem-4-carboxylic acid
THF=tetrahydrofuran
DBN=1,5-diaza-bicyclo[4.3.0]non-5-ene
DBU=1,8-diaza-bicyclo[5.4.0]undec-7-ene

EXAMPLE 1

Salt of 7-amino-3-hydroxymethyl-3-cephem-4-carboxylic acid with tetramethylguanidine 1 g of HACA are suspended in 3 ml of dichloromethane. After addition of 1.2 equivalents of tetramethyl guanidine a solution is obtained within 5 minutes at room temperature. To this solution ca. 5 ml of methyl tert.butyl ether are added, whereby a sirupy deposit is formed. The supernatant solution is decanted off, the residue digested with methyl tert-.butyl ether and dried. The title compound is obtained as a syrup.

EXAMPLE 2

Salt of 7-amino-3-hydroxymethyl-3-cephem-4-carboxylic acid with tetramethylguanidine 23 g of HACA are suspended in 130 ml of dichloromethane. After addition of 1.2 equivalents of tetramethyl guanidine a solution is obtained within ca. 30 minutes at 0°. This solution is cooled to −25° and inoculated. The title compound crystallizes and is filtered off. The crystals are washed with cold dichloromethane and dried.

Melting point: 150°–154° (Decomposition).

In analogous manner to that described in the preceding Examples, as appropriate, the following HACA salts are obtained:

| Example | Salt | |
|---|---|---|
| 3 | DBU | syrup |
| 4 | DBN | M.p.: 143–146° (decomp.) |

The salts according to the invention may be used to produce cephalosporin end products, e.g. the following of which are produced:

EXAMPLE 5

Production of 7β-((Z)-(2-amino-1,3-thiazol-4-yl)-2-methoximinoacetamido)-3-hydroxymethyl-3-cephem-4-carboxylic acid a) Production using the salt of HACA with tetramethylguanidine 18.4 g of HACA are suspended in 120 ml of methanol and the suspension is cooled to 0°. After addition of 10.6 ml of tetramethylguanidine a clear solution is obtained within ca. 5 minutes. To this solution 30.8 g of (Z)-2-aminothiazol-4-yl-methoximinoacetic acid-2-mercaptobenzthiazolylester are added in portions and the mixture is stirred for 4 hours at 0°. 120 ml of water are added dropwise. The mercaptobenzthiazole which is released slowly precipitates. After filtration the mother liquor is slowly adjusted to pH 3.5. The suspension formed is stirred for 1 hour in an ice bath. The product crystallizes, is filtered off, washed with cold methanol and dried.

b) Production using the salt of HACA with DBU 23.0 g of HACA are suspended in 250 ml of dichloromethane. After addition of 15 ml of DBU and of 25 ml of methanol whilst stirring and cooling with ice, and within ca. 15 minutes a practically clear solution is obtained. After addition of 38.6 g of (Z)-2-aminothiazol-4-yl-methoximinoacetic acid-2-mercaptobenzthiazolylester the suspension is stirred for 2.5 hours. HPLC analysis shows that the starting material is completely reacted. The reaction mixture is diluted with 100 ml of water, the phases are separated and the dichloromethane phase is washed with 25 ml of saturated bicarbonate solution. The combined aqueous solutions are re-extracted with dichloromethane. The pH of the aqueous phase is adjusted to 3 with aqueous hydrochloric acid. The title compound precipitates as a raw product. The raw product is suspended in 170 ml of water, dissolved with 2N NaOH at pH 7 and the mixture is treated with 7 g of active carbon. After filtration, the aqueous phase is mixed with its half volume of ethanol, and the pH of the solution is adjusted to pH 3 with hydrochloric acid. The title compound precitipates, is filtered off, washed with 50 ml of water and dried.

EXAMPLE 6

Production of 7β-((Z)-2-(24-tert-butoxycarbonylaminothiazol-4-yl)-2-pentenoyl)-amino-3-carbamoyloxymethyl-3-cephem-4-carboxylic acid diisopropylamine salt a) Production using the salt of HACA with tetramethylguanidine 13.8 g of HACA are suspended in 90 ml of dichloromethane. After addition of 9.1 ml of tetramethylguanidine a practically clear solution is obtained within ca. 5 minutes which is cooled to –20°. This solution is added to the mixed anhydride of (Z)-2-(2-tert-butoxycarbonylaminothiazol-4-yl)-2-pentenecarboxylic acid and methanesulphonic acid, produced by reacting 19.3 g of (Z)-2-(2-tert-butoxycarbonylaminothiazol-4-yl)-2-pentenoic acid and 5.55 ml of methanesulphonic acid chloride in 195 ml of methylene chloride in the presence of 11.8 ml of diisopropylamine at –15°. The temperature is held at about –10°. Simultaneously 5.1 ml of diisopropylamine are added in order to neutralize the methanesulphonic acid being released. After addition, the reaction mixture is stirred for a further 30 minutes at a temperature of less than –10°. The mixture is cooled to about –40° and 3.2 ml of methanesulphonic acid in 30 ml of dichloromethane are added over the course of 10 minutes, followed by 7.3 ml of chlorsulphonyl isocyanate. The temperature is kept below –40° C. The mixture is subsequently stirred for 30 minutes at the above temperature. The reaction mixture is mixed with a mixture of 90 ml of dimethylformamide and 250 ml of water and the emulsion is heated for ca. 3 hours to 30°. After phase separation the organic phase is extracted with 200 ml of water. To the methylene chloride phase 8.4 ml of diisopropylamine are added. The title compound precipitates. The product suspension is stirred for another 30 minutes, the product is isolated through a suction filter, washed with methylene chloride and dried.

b) Production using the salt of HACA with DBU 2.3 g of HACA are suspended in 30 ml of dichloromethane. After addition of 3.0 ml of DBU a practically clear solution is obtained within 5 minutes. This solution is cooled to –20° and added slowly to a solution of the mixed anhydride of (Z)-2-(2-tert. butoxycarbonylaminothiazol-4-yl)-2-pentenecarboxylic acid (BAPA) and methanesulphonic acid, produced by reacting 3.43 g of BAPA and 0.98 ml of methanesulphonic acid chloride in 68 ml of dichloromethane in the presence of 2.1 ml of diisopropylamine. The temperature is held at about –10°. The mixture is stirred for a further 30 minutes at a temperature of less than –10°. HPLC analysis shows that the reaction is practically completed. The mixture is cooled to –50° and 0.62 ml of methanesulphonic acid, followed by 1.4 ml of chlorosulphonyl isocyanate are added. After 15 minutes HPLC analysis shows that the reaction is practically completed.

$^1$H-NMR Spectra (300 MHz, CDCl$_3$)

Example Spectrum:

1,2 4.90 (d, J=5.0 Hz, 1H, H-6), 4.78 (d, J=5.0 Hz, 1H, H-7), 4.45 (d, J=12.3 Hz, 1H, C$\underline{H}$H'—OH), 3.77 (d, J=12.3 Hz, 1H, CH$\underline{H}$'—OH), 3.51 and 3.46 (AB, J=17.8 Hz, 2H, CH$_2$—S), 2.99 (s, 12H, 4×CH$_3$—N)

3 4.90 (d, J=5.0 Hz, 1H, H-6), 4.78 (s broad, 1H, H-7), 4.45 (d, J=12.3 Hz, 1H, C$\underline{H}$H'—OH), 3.72 (d, J=12.3 Hz, 1H, CH$\underline{H}$'—OH), 3.60 to 3.35 (m, 8H, CH$_2$—S, 3×CH$_2$—N), 2.85 (s broad, 2H, CH$_2$—C=), 2.10 (qi, J=57 Hz, 2H, —CH$_2$—), 1.9 to 1.5 (m, 8H, 3×—CH$_2$—, —NH$_2$)

4 4.90 (d, J=5.0 Hz, 1H, H-6), 4.78 (d, J=5.0 Hz, 1H, H-7), 4.40 (d, J=12.3 Hz, 1H, C$\underline{H}$H'—OH), 3.71 (d, J=12.3 Hz, 1H, CH$\underline{H}$'—OH), 3.64 to 3.42 (m, 6H, CH$_2$—S, 2×CH$_2$—N), 3.37 (t, J=6.0 Hz, 2H, CH$_2$—N), 3.20 (m, 2H, CH$_2$—C=), 2.16 (qi, J=7.9 Hz, 2H, —CH$_2$—), 2.04 (qi, J=5.9 Hz, 2H, —CH$_2$—)

What we claim is:

1. A compound of the formula

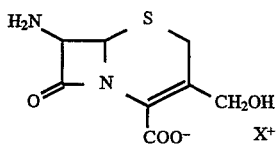   I wherein $X^+$ is a compound of the formula

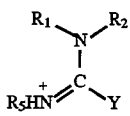   II wherein Y is
(i) a group of the formula —$NR_3R_4$ and
  a) $R_1$, $R_2$, $R_3$, $R_4$, and $R_5$ are each independently hydrogen; ($C_1$–$C_8$)alkyl unsubstituted or substituted by phenyl, nitro, protected hydroxy, protected thio, or protected amino; phenyl unsubstituted or substituted by ($C_1$–$C_8$)alkyl, phenyl, protected hydroxy, protected thio, halogen, nitro, or protected amino, or
  b) two of the substituents $R_1$, $R_2$, $R_3$, $R_4$, and $R_5$ bonded to different nitrogen atoms form a —$(CH_2)_2$— or —$(CH_2)_3$— group and the other substituents are as defined above, or
(ii) Y together with $R_2$ is a —$(CH_2)_3$— or —$(CH_2)_5$— group and $R_1$ and $R_5$ together is a —$(CH_2)_3$— group.

2. A compound according to claim 1 in which $R_1$, $R_2$, $R_3$, $R_4$, and $R_5$ are each independently hydrogen, methyl, ethyl, benzyl, or phenyl.

3. A compound of according to claim 1, wherein Y is a group of formula —$NR_3R_4$ and $R_1$ to $R_5$ are the same or different and are independently of one another hydrogen, ($C_1$–$C_8$)alkyl, benzyl or phenyl.

4. A compound according to claim 1 in which Y together with $R_2$ is a —$(CH_2)_3$— or —$(CH_2)_5$— group and $R_1$ and $R_5$ together is a —$(CH_2)_3$— group.

5. A compound according to claim 1 which is the salt of 7-amino-3-hydroxymethyl-3-cephem-4-carboxylic acid with
  (a) tetramethylguanidine,
  (b) 1,8-diaza-bicylo-(5.4.0)undec-7-ene, (or)
  (c) 1,5-diaza-bicylo-(4.3.0)non-5-ene.

6. A process for the production of a cephalosporin compound comprising:
  (i) acylating 7-amino-3-hydroxymethyl-3-cephem-4-carboxylic acid in the form of an amidine salt of formula (I) according to claim 1 at the amine group in position 7; and, where necessary,
  (ii) converting the acylated product of (i) into another cephalosporin compound.

7. A process according to claim 6 in which the 7-amino group of the compound is acylated with (Z)-2-aminothiazol-4-yl-2-methoxyiminoacetic acid, 2-mercaptobenzthiazolyl ester.

8. A process according to claim 6 in which the 7-amino group of the compound is acylated with mixed anhydride of (Z)-2-(2-tert-butoxycarbonylaminothiazol-4-yl)-2-pentene-carboxylic and methanesulphonic acid.

9. A process according to claim 6 in which the reaction is carried out in an aprotic solvent.

10. A process according to claim 6 in which the reaction is carried out in a protic solvent.

11. A process according to claim 6 in which the reaction is carried out in dichloromethane, methanol, or acetonitrile.

12. A process for according to claim 6 which comprises converting the product into a cephalosporin derivative by reacting the 3-hydroxymethyl group.

* * * * *